United States Patent
Oura et al.

(10) Patent No.: US 9,304,088 B2
(45) Date of Patent: Apr. 5, 2016

(54) METHOD AND APPARATUS FOR MEASURING PH OF SOLUTION

(75) Inventors: Mitsuhiro Oura, Tokyo (JP); Teruo Okano, Tokyo (JP); Tatsuya Shimizu, Tokyo (JP); Hirotsugu Kubo, Tokyo (JP); Sunao Takeda, Tokyo (JP); Shinji Yamamori, Tokyo (JP)

(73) Assignees: NIHON KOHDEN CORPORATION, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 997 days.

(21) Appl. No.: 13/400,106

(22) Filed: Feb. 19, 2012

(65) Prior Publication Data

US 2012/0214250 A1 Aug. 23, 2012

(30) Foreign Application Priority Data

Feb. 18, 2011 (JP) ................................ 2011-033371

(51) Int. Cl.
| | |
|---|---|
| *G01N 21/80* | (2006.01) |
| *G01N 31/22* | (2006.01) |
| *G01N 21/31* | (2006.01) |
| *C12M 1/34* | (2006.01) |

(52) U.S. Cl.
CPC ............. *G01N 21/80* (2013.01); *C12M 41/26* (2013.01); *G01N 21/3151* (2013.01); *G01N 31/221* (2013.01); *G01N 2201/0627* (2013.01); *G01N 2201/1211* (2013.01)

(58) Field of Classification Search
CPC .............................. G01N 21/80; G01N 31/221
USPC ........................................... 436/163; 422/82.9
See application file for complete search history.

(56) References Cited

U.S. PATENT DOCUMENTS

| 4,033,330 A | | 7/1977 | Willis et al. | |
|---|---|---|---|---|
| 4,200,110 A | * | 4/1980 | Peterson et al. | ............. 600/367 |
| 5,888,395 A | * | 3/1999 | Carman et al. | ................ 210/606 |

(Continued)

FOREIGN PATENT DOCUMENTS

| CN | 1366184 A | 8/2002 |
|---|---|---|
| CN | 101738336 A | 6/2010 |

(Continued)

OTHER PUBLICATIONS

The extended European Search Report for the related European patent application No. 12155967.8 dated Nov. 9, 2012.

(Continued)

*Primary Examiner* — Christopher A Hixson
*Assistant Examiner* — Emily Berkeley
(74) *Attorney, Agent, or Firm* — Kenealy Vaidya LLP

(57) ABSTRACT

A method of measuring a pH of a solution includes: emitting light beams of two wavelengths from one side of a measuring region of a solution into which an indicator is mixed, while pulsating the solution in the measuring region; receiving at least one of transmitted light beams and reflected light beams of the emitted light beams on the other side of the measuring region, while pulsating the solution in the measuring region; obtaining absorbances of the two wavelengths based on the received at least one of the transmitted light beams and the reflected light beams; obtaining an absorbance ratio from the obtained absorbances; and calculating a pH value of the solution based on the obtained absorbance ratio and an absorbance ratio/pH value correspondence database which is previously stored.

8 Claims, 7 Drawing Sheets

(56) References Cited

U.S. PATENT DOCUMENTS

| | | |
|---|---|---|
| 2008/0188722 A1 | 8/2008 | Markle et al. |
| 2008/0318307 A1* | 12/2008 | Spittle et al. ............... 435/288.7 |
| 2010/0151512 A1 | 6/2010 | Huemer |

FOREIGN PATENT DOCUMENTS

| | | |
|---|---|---|
| DE | 195 30 183 A1 | 2/1997 |
| EP | 0 759 549 A1 | 2/1997 |
| JP | 52-64184 A | 5/1977 |
| JP | 62-115297 A | 5/1987 |
| JP | 6-34754 A | 5/1994 |
| JP | 2004-92537 A | 3/2004 |
| JP | 2009-533053 A | 9/2009 |

OTHER PUBLICATIONS

Japanese Office Action for the related Japanese Patent Application No. 2011-033371 dated Apr. 21, 2015.

Chinese Office Action for the related Chinese Patent Application No. 201210039189.6 dated Apr. 10, 2015.

* cited by examiner

METHOD AND APPARATUS FOR MEASURING PH OF SOLUTION

BACKGROUND OF THE INVENTION

The present invention relates to a method and apparatus for measuring the pH of a cell culture solution.

In order to grow and proliferate cells, the pH of a culture solution containing the cells must be within a range suitable for proliferation. During preparation or storage of such a cell culture solution, however, carbon dioxide which is contained in the cell culture solution is released, and the pH is increased, so that the pH is often deviated from the proliferation suitable range.

Therefore, the pH is measured by a method in which, for example, the color change of phenol red that is usually contained in a cell culture solution is visually checked, or that in which the measurement is performed while pH electrodes are immersed in a cell culture solution. However, these methods have the following problems.

In the case where the color change of phenol red contained in a cell culture solution is visually checked, an erroneous check may be caused. By contrast, in the case where pH electrodes are immersed in a cell culture solution, when the pH electrodes are not sufficiently sterilized, contamination due to bacteria or the like may occur.

As a method of measuring the pH of a cell culture solution which is free from problems such as an error due to a visual check, and contamination in the case where pH electrodes are used, there is the following method (see JP-B-6-34754).

JP-B-6-34754 describes the followings.

A pH measuring method is provided which is a method of measuring the pH of a cell culture solution in which the pH is measured based on absorption of visible light in a cell culture solution that includes: a cell culture medium; serum; and an indicator having two or more kinds of absorption peaks in the wavelength region of visible light, wherein, based on a linear relationship between the pH and the logarithms of absorbances at two wavelengths of absorption peaks that are obtained by transmitting visible light through a cell culture solution in which the pH is known, the value of the pH is obtained from the value of the logarithm of a ratio of absorbances of absorption peaks that are measured in a cell culture solution specimen in which the pH is not known.

Furthermore, a pH measuring method is provided which is a method of measuring pH of a cell culture solution in which the pH is measured based on absorption of visible light in a cell culture solution that includes: a cell culture medium; serum; and an indicator having two or more kinds of absorption peaks in the wavelength region of visible light, wherein, based on a linear relationship between the pH and the logarithms of a ratio of differences between absorbances at two wavelengths of absorption peaks that are obtained by transmitting visible light through a cell culture solution in which the pH is known, and an absorbance at a wavelength where absorption peaks do not exist, the value of the pH is obtained from the value of the logarithm of a ratio of a difference of similar absorbances that are measured in a cell culture solution specimen in which the pH is not known.

The method of measuring the pH of a cell culture solution is characterized in that a cell culture solution that includes: a cell culture medium; serum such as fetal bovine serum; and an indicator, is poured into a transparent container, the cell culture solution is irradiated with visible light, and the pH is calculated from the transmission spectrum or reflection spectrum.

In a cell culture solution, usually, phenol red for detecting a change of the pH is contained at a low concentration which does not harm cells. In the visible light range, at such a low concentration, phenol red has peaks in the vicinities of 430 to 440 nm and 560 nm, and an isosbestic point at 480 nm. In a pH range of 6.8 to 7.6 where cells can grow, as the pH is further lowered, the absorption peak in the vicinity of 430 to 444 nm is more increased, and that in the vicinity of 560 nm is more decreased. When absorption due to only the phenol red is obtained, by taking a ratio of absorption in the vicinity of 430 to 440 nm to that in the vicinity of 560 nm, the plot shows one curve, and the pH of the culture solution can be calculated from a ratio of the two peaks.

The following is known as a reference example of a technique in which two parameters, i.e., the temperature and pH of the culture medium that are important for, in cell culture such as in artificially fertilized cell culture, regulating the environment to ensure healthy cell growth are monitored (see JP-T-2009-533053).

The embodiment in the reference example shown in FIG. 9 includes an incubator 202 having trays 204 upon which culture dishes 206 are carried. Other culture vessels such as flasks may be used. Moreover, the incubator may be of any size or construction. Each culture dish is accompanied by a pH sensor and a temperature sensor associated with a cuvette 208 of a medium. The sensors perform measurements of the pH and temperature of the medium in the cuvette and hence of the pH and temperature of the media in the culture dish without the need for the light sensors and thermocouple to be directed into the culture dish. Hereinafter, these units are referred to as "reader units". In the embodiment, the reader units optically perform the pH measurement by using light emitting diodes (LEDs) as a light source, and the temperature measurement by using the thermocouple.

An embodiment of the reader units includes a fully sealed unit so that it can withstand spillages, with packaging made from a suitable plastic which can be cleaned and sterilized. In other cell culture applications using large dishes or flasks, it may be possible to immerse the unit in the actual solution being monitored. In this case, if phenol red is not dissolved in the solution, an optode with an immobilized indicator may be used. The reader unit may be either re-chargeable, or have a battery which either lasts a sufficiently long time, or is replaceable.

The reader unit 210 has a wireless communication capability with respect to a slave receiver/transmitter unit 212. The slave receiver/transmitter unit 212 is connected wirelessly to a data logger 214 which records the data from the reader units. The data logger 214 has a download capability with respect to a computer system 216 which displays and stores the details of the temperature and the pH. Alternatively, the slave receiver/transmitter unit 212 may be hard wired to the data logger 214.

The complete system is modular and expandable. A central data logger is a repository of data and can accommodate the data streams from multiple readers. The data are downloadable to a PC, and a suitable piece of software for downloading and presenting the data forms part of the system. Reader units can be used to monitor the conditions in an incubator and control feedback, but the use of a reader per culture vessel enables tracking of the history of the individual culture vessels. When the vessel is outside the incubator for inspection, medium changes, etc., it is most susceptible to variations in temperature and pH, so this is really the crucial time to monitor the situation. In such a situation, the reader unit 210a can transmit wirelessly directly to the data logger 214.

Since much of the culture cycle will be spent inside a metal clad incubator, it is envisaged that a slave receiver/transmitter can be placed inside or outside the incubator to receive the wireless signals from the units during these periods. This unit can be connected to a main logger unit situated outside the incubator and may be connected wirelessly or be hard wired. Alternatively, the reader unit may be hard wired to the data logger or the data logger may have antennae which are inserted into the incubator (thereby removing the need for slave receiver/transmitter units). Since the embodiment is one where there is a central data logger receiving data from multiple incubators (and multiple dishes therein), however, greater flexibility would be provided by having a slave receiver/transmitter unit with each incubator. If the incubators are clad in a material which transmits radio signals, the receiver/transmitter can also directly transmit to the logger unit.

When the culture dish 206a is outside the incubator 202, therefore, the reader unit 210a can transmit directly to the data logger 214.

In the case where the reader unit is being used to monitor the history of an individual vessel, it needs to stay associated with that vessel, and a holder can be used which holds both the vessel and reader unit so that they can be transported about together.

In the embodiment, the reader units wirelessly transmit data. Whilst, inside the incubator, the data will be received by the slave unit. The main logger unit also looks for the data stream, and does not receive it when the units are outside the incubator, the slave units will not receive the signals through the metal cladding of the incubator. Alternatively, the slave receiver/transmitter unit may be placed on the outside of the incubator with an antenna inside and outside the incubator so that it always receives the signal. In order to conserve power while the reader unit is in the incubator, the reader unit may not transmit data continuously, but at a pre-determined time interval. When the reader unit is once outside the incubator, the reader can perform transmission more frequently since this is the time when changes are likely to occur more rapidly. One way of causing the reader to know that it is outside the incubator is to use a photodiode and look for changes in ambient light. Inside the incubator, it will generally be dark. The reader units will also have warning indicators which, when the pH or the temperature starts to go outside of the acceptable range, warn that the vessel should be put back in the incubator. If the cycle is complete and/or the dish is left out for a long period of time, the unit may revert back to a slower period of sampling.

In the embodiment, the reader uses three wavelengths in the optical measurement (more than three could also be used). Two of these wavelengths are used to determine the pH from the ratio of acid and base form concentrations of the indicator. This is determined by using the absorption coefficients of the acid and base forms of the indicator, and solving simultaneous equations for the absorption at the two wavelengths. Using a ratio makes the measurement relatively independent of the actual amount of the indicator added to the cuvette. Since the apparatus is to be as low cost as possible, it is another aspect of the reference example to incorporate a method of auto zeroing. In optical measurements, usually, a zero level measurement is performed with a sample blank prior to measuring the sample. The absorption levels of the blank are then subtracted from the sample reading to provide the net absorbance of the sample. In the apparatus, the third wavelength is chosen such that it shows very little absorption by the indicator, and is used as means of tracking changes in the zero level. Changes in the absorption level of this wavelength channel are then indicative of changes in the zero level, and the other two wavelengths which are used in the measurement can be zero corrected based on the changes measured at this third wavelength. This will correct for variations arising due to offsets, for example arising from different wall thickness cuvettes or coatings depositing out of solution onto the cuvette walls.

Another factor which affects the zero level is the temperature of the LEDs. Experiments have shown that the intensities of the three wavelengths vary with temperature, but not by the same absolute amount. A simple factory calibration of the apparatus provides coefficients for the relationship between the different wavelength LEDs. Any shift in the absorbance level of the third wavelength is due to effects of offsets (as described above) and temperature drift. The measured temperature can be used to calculate the thermal drift component, and the remainder of any change in the zero level of the third wavelength will be due to offset effects. The offset and temperature drift corrections can then be determined and applied to the other two wavelengths used in determining the pH.

FIG. 10 shows one embodiment the of reader unit according to the reference example. The reader unit 220 has a reader body 221 and a gripper 222 for receiving and retaining a culture vessel 224. The gripper may be of any convenient size to grip and carry a culture vessel. For example, the gripper is made of silicone elastomer, and sized to grip and retain a 35-mm culture dish. This enables a culture dish to be transported with the reader unit to enable monitoring to be continued outside the incubator.

The reader body 221 includes a recess 226 for a cuvette 228 to carry a sample of the fluid which is the same as that in the culture dish as discussed above.

Within the reader body, as shown in FIG. 11, there is an LED light source arrangement 230 comprised of three or more LEDs of different frequencies as discussed above directed to a light guide 232 so that the light beam passes across the slot 226 to an LED receiver assembly 236. The LED receiver assembly 236 includes receivers for each of the frequencies of the LED light source arrangement. Electronic circuitry 238 processes the various readings, and a battery 239 (underneath the electronic circuitry and shown by the broken line) makes the reader unit self-contained. Adjacent to the light source 230 is a second LED receiver 240 which measures and compensates for drift in the transmitting LED assembly 230 emitting light. An aerial 242 associated with the electronic circuitry transmits readings to a data logger within the incubator or to a monitoring device outside the incubator. The reader unit also includes a thermocouple 244 for measuring the temperature, and the electronic circuitry 238 can transmit temperature data as well as pH data.

A version of the reader unit as shown in FIGS. 10 and 11 may be supplied without the gripper. Such an apparatus can be used to monitor a whole incubator chamber and act as a warning device, setting off an alarm when the pH or the temperature moves outside preset limits.

As described above, in the related-art optical pH measurement, the zero level measurement is performed with a sample blank prior to measuring the sample, and the absorption levels of the blank are then subtracted from the sample reading to provide the net absorbance of the sample. The vicinity of the wavelength (700 nm) which shows very little absorption by the indicator is chosen as the third wavelength, and is used as means for tracking changes in the zero level. Changes in the absorption level of this wavelength channel are indicative of changes in the zero level. Therefore, the other two wavelengths which are used in the measurement must be zero corrected based on the changes measured at this third wavelength.

SUMMARY

It is therefore an object of the invention to provide a method of measuring the pH of a solution in which it is not necessary to correct the zero level due to a wavelength in the vicinity of 700 nm that shows very little absorption by an indicator, and also an apparatus for measuring pH of a cell culture solution.

In order to achieve the object, according to the invention, there is provided a method of measuring a pH of a solution comprising: emitting light beams of two wavelengths from one side of a measuring region of a solution into which an indicator is mixed, while pulsating the solution in the measuring region; receiving at least one of transmitted light beams and reflected light beams of the emitted light beams on the other side of the measuring region, while pulsating the solution in the measuring region; obtaining absorbances of the two wavelengths based on the received at least one of the transmitted light beams and the reflected light beams; obtaining an absorbance ratio from the obtained absorbances; and calculating a pH value of the solution based on the obtained absorbance ratio and an absorbance ratio/pH value correspondence database which is previously stored.

One of the light beams may have a wavelength of 400 to 460 nm, and the other of the light beams may have a wavelength of 530 to 580 nm.

According to the invention, there is also provided an apparatus for measuring a pH of a solution comprising: a light beam emitting unit configured to emit light beams of two wavelengths from one side of a measuring region of a solution into which an indicator is mixed; a light beam receiving unit configured to receive at least one of transmitted light beams and reflected light beams of the emitted light beams on the other side of the measuring region; a solution pulsating unit configured to perform pulsation of the solution in the measuring region; an absorbance calculating unit configured to obtain absorbance of the two wavelengths based on the at least one of the transmitted light beams and the reflected light beams which are received by the light beam receiving unit during the pulsation of the solution by the solution pulsating unit; an absorbance ratio calculating unit configured to obtain an absorbance ratio from the obtained absorbances; and a pH value calculating unit configured to calculate a pH value of the solution based on the obtained absorbance ratio and an absorbance ratio/pH value correspondence database which is previously stored.

The solution pulsating unit may perform the pulsation of the solution existing between the light beam emitting unit and light beam receiving unit.

The solution pulsating unit may be one of a peristalic pump, a syringe pump, and a centrifugal pump, placed in front of or in back of the measuring region of the solution.

The solution pulsating unit may perform the pulsation at a frequency at which pulsation can be detected.

The solution pulsating unit may perform the pulsation only when the pH is to be measured.

The solution pulsating unit may change a distance between the light beam emitting unit and light beam receiving unit.

DETAILED DESCRIPTION OF EMBODIMENTS

First, the principle of the pH measurement due to two wavelengths which is the premise of the apparatus for measuring the pH of a solution according to the invention (hereinafter, the apparatus is often referred to as the solution pH measuring apparatus), and in which phenol red is used as a pH indicator, will be described.

Figure 3:
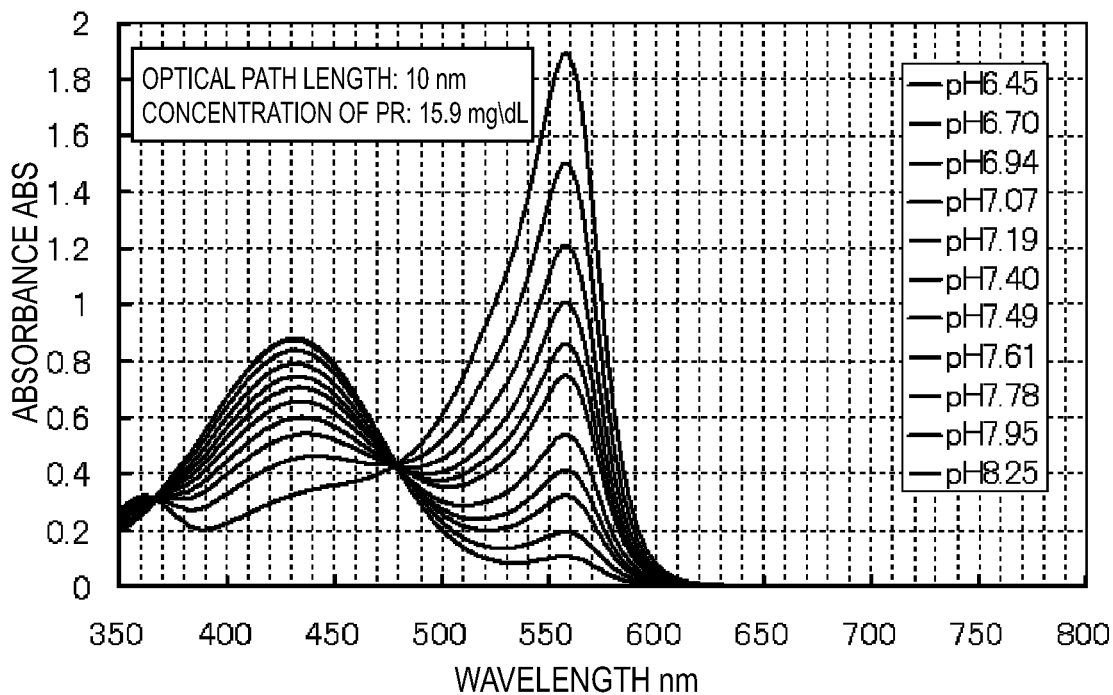
FIG. 3 is a view showing the absorbance of phenol red at wavelengths of 300 to 700 nm, at pH of 6.45 to pH of 8.25.

FIG. 3 is a view showing the absorbance of phenol red at wavelengths of 300 to 700 nm, at pH of 6.45 to pH of 8.25.

As shown in FIG. 3, peaks exist in the vicinities of 430 and 558 nm, and the absorbance is substantially zero in the vicinity of the wavelength of 700 nm.

When it is assumed that there is no scattering, the followings are obtained from the Lambert-Beer law.

$A_{558} = \alpha_{558} L C$ $A_{430} = \alpha_{430} L C$ where $\alpha$: absorption coefficient L: optical path length C: concentration Therefore, the absorbance ratio is expressed as follows.

$$A_{558}/A_{430} = \alpha_{558} L C / \alpha_{430} L C = \alpha_{558}/\alpha_{430}$$

Figure 4:
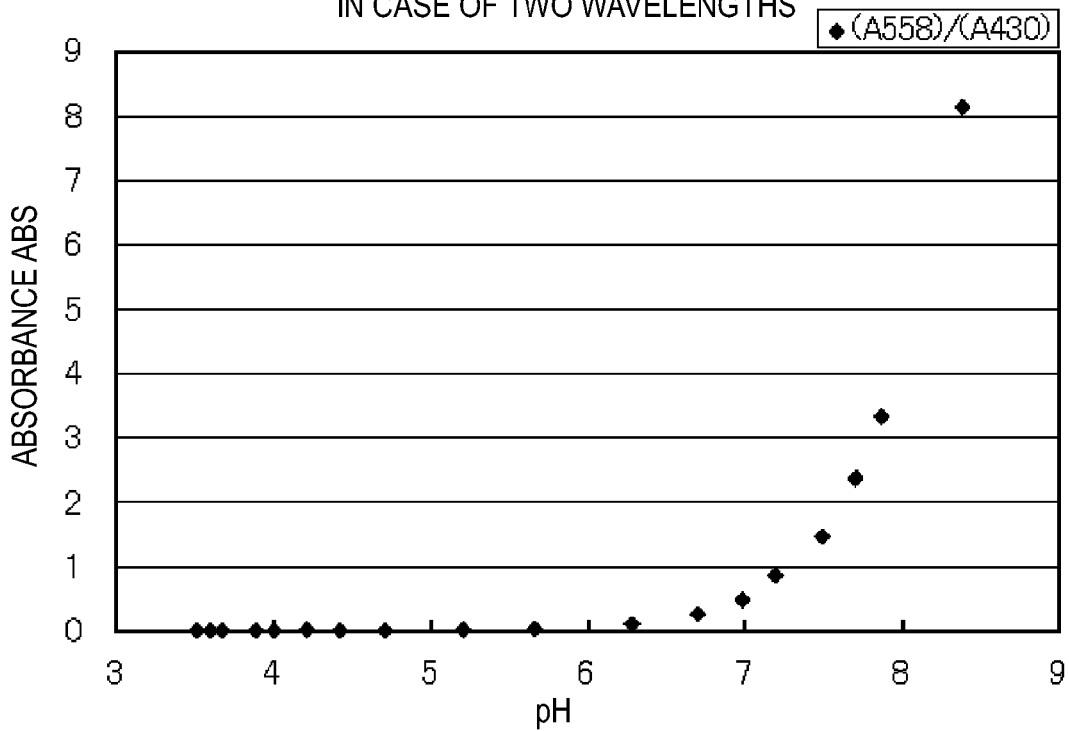
FIG. 4 is a view showing relationships between an absorbance ratio (A558/A430) and the pH.

The absorbance ratio (A558)/(A430) and the pH have the relationships shown in FIG. 4.

Figure 5:
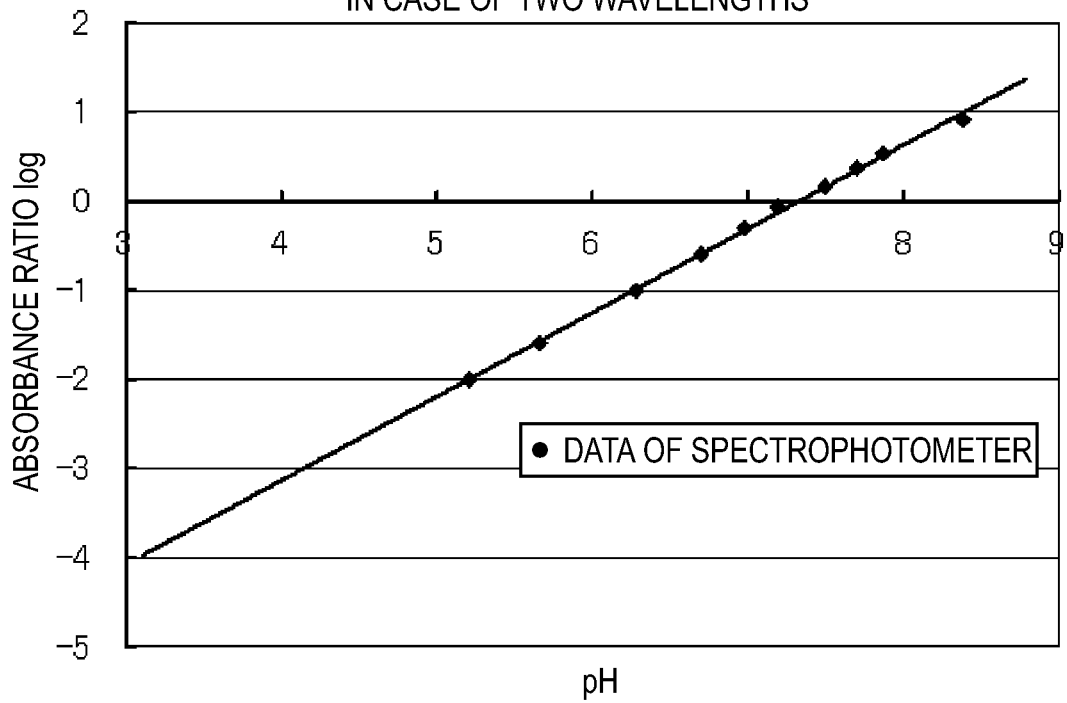
FIG. 5 is a view showing relationships between an absorbance ratio log (A558/A430) and the pH.

The absorbance ratio log (A558)/(A430) and the pH have the relationships shown in FIG. 5.

In the case of the absorbance ratio log (A558)/(A430), the relationships with the pH can be substantially approximated by a straight line.

In the case where the zero level correction is performed at the wavelength of 700 nm functioning as the reference (the absorbance is zero), the absorbance ratio of the wavelength of 558 nm to that of 430 nm does not change even when the concentration of phenol red and the optical path length are changed.

Next, the apparatus and method of measuring the pH of a solution according to the invention will be described with reference to FIGS. 1 and 2.

Figure 1:
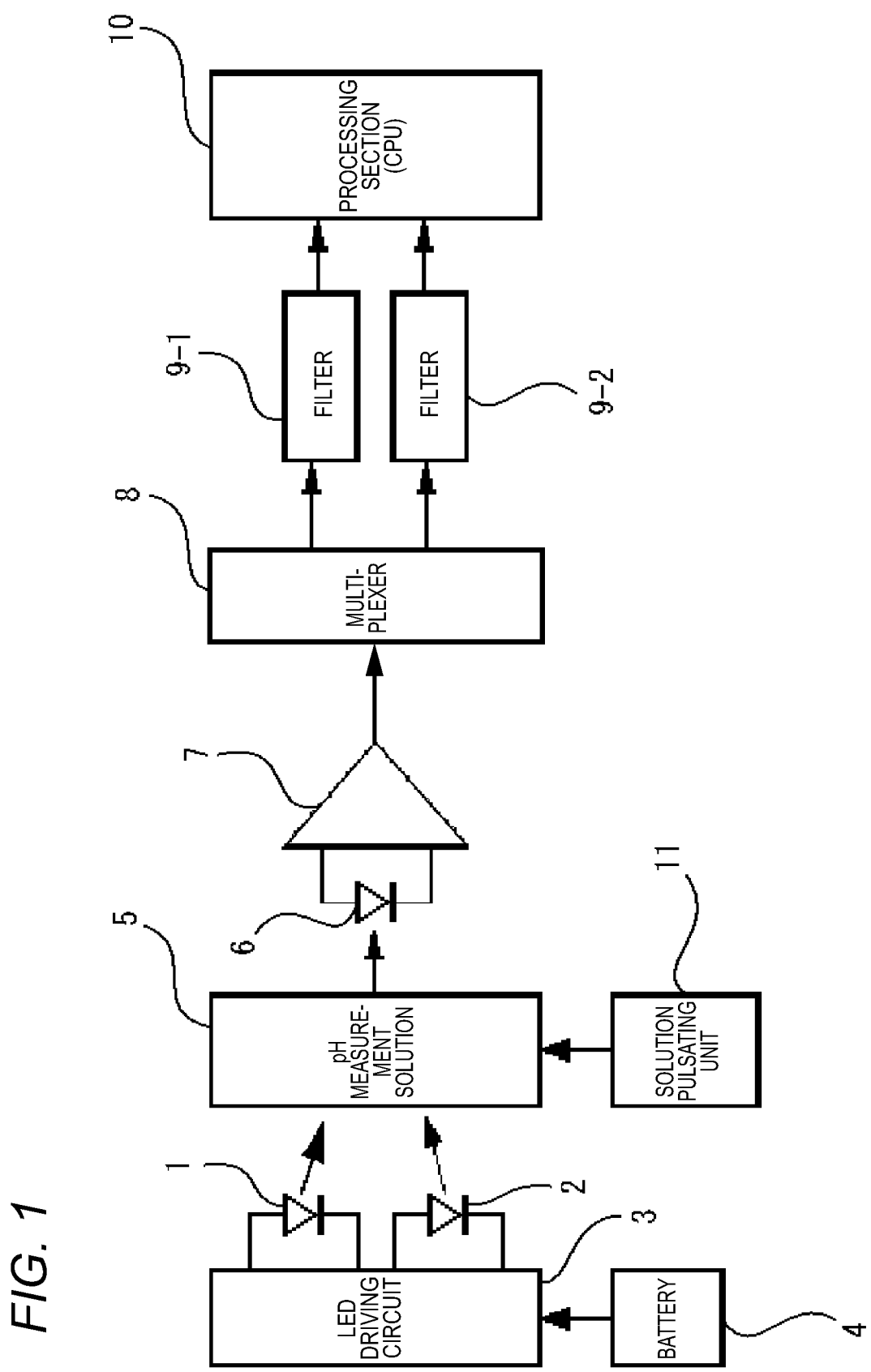
FIG. 1 is a block diagram showing the basics of the apparatus for measuring the pH of a solution according to the invention.
Figure 2:
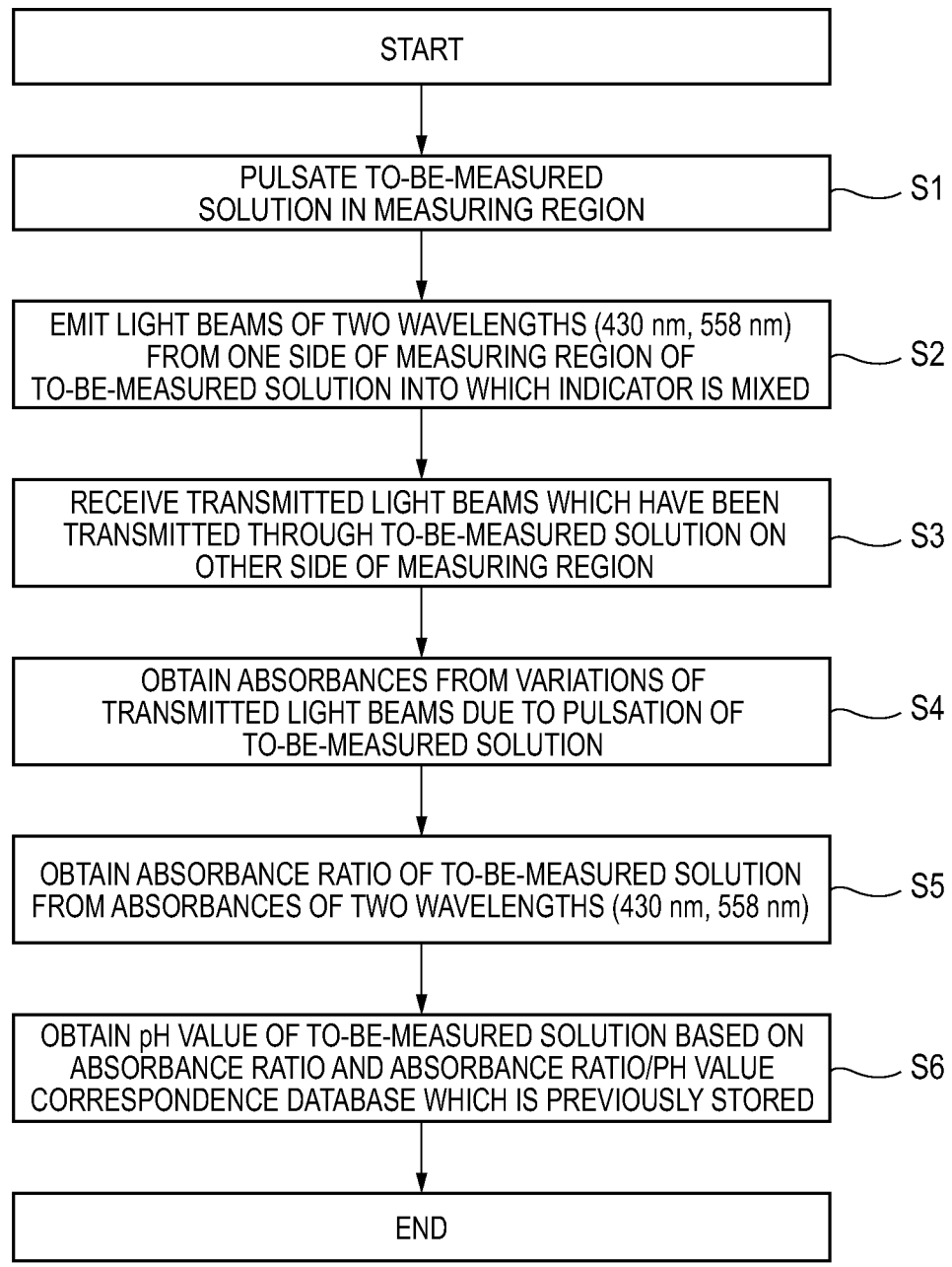
FIG. 2 is a flowchart showing the procedure of measuring the pH of a solution by the apparatus for measuring the pH of a solution according to the invention.

FIG. 1 is a block diagram showing the basics of the solution pH measuring according to the invention.

Light emitting elements (LEDs) 1, 2 which emit light beams of different wavelengths are driven by a driving circuit 3 so as to alternately emit the light beams by using an electric power supplied from a battery 4.

As the light beams of the light emitting elements 1, 2, those of wavelengths of 430 [nm] and 558 [nm] which indicate absorbance peaks are employed, respectively. However, the wavelengths are not limited to them. Specifically, it is preferable that one of the wavelengths shows an absorbance peak between 400 nm and 460 nm (preferably, between 420 nm and 440 nm), and the other shows an absorbance peak between 530 nm and 580 nm (preferably, between 540 nm and 580 nm).

The light beams emitted from the light emitting elements 1, 2 are transmitted through a solution 5 in which the pH is to be measured, and then received by a photodiode 6 which is a light receiving element, to be converted to electric signals.

In FIG. 1, the light receiving element is configured by one element. Alternatively, two light receiving elements may be disposed opposingly to the two light emitting elements.

Alternatively, reflected light beams may be received.

The converted signals are amplified by an amplifier 7, and then distributed by a multiplexer 8 to filters 9-1, 9-2 which correspond to the light wavelengths, respectively.

The signals distributed to the filters 9-1, 9-2 are filtered by the filters to reduce noise components, digitized by an A/D converter which is not shown, and then supplied to a processing section (CPU) 10.

A solution pulsating unit 11 is a unit for physically pulsating the distance (in the figure, the to-be measured solution in a pH measuring vessel) between the unit for emitting the light beams of the two wavelengths and that for receiving the light beams.

Next, the measurement of the pH of a solution by the solution pH measuring apparatus of the invention will be described with reference to the flowchart of FIG. 2.

In the solution 5 into which an indicator (phenol red) is mixed, the solution in a measuring region is pulsated by the solution pulsating unit 11 (step S1).

The light emitting diodes (LEDs) which are placed on one side of the measuring region of the solution 5 are alternately driven to emit light beams of two wavelengths (430 nm, 558 nm) (step S2).

The light receiving element (PD) which is placed on the other side of the measuring region receives transmitted light beams which have been transmitted through the solution 5 (step S3).

Absorbances are obtained from variations of the transmitted light beams due to the pulsation of the solution 5 which is caused by the solution pulsating unit 11 (step S4).

An absorbance ratio is obtained from the absorbances of the light beams of the two wavelengths which are calculated in the absorbance calculating step (step S5).

The value of the pH of the solution is obtained based on the absorbance ratio and an absorbance ratio/pH value correspondence database which is previously stored (step S6).

Figure 6:
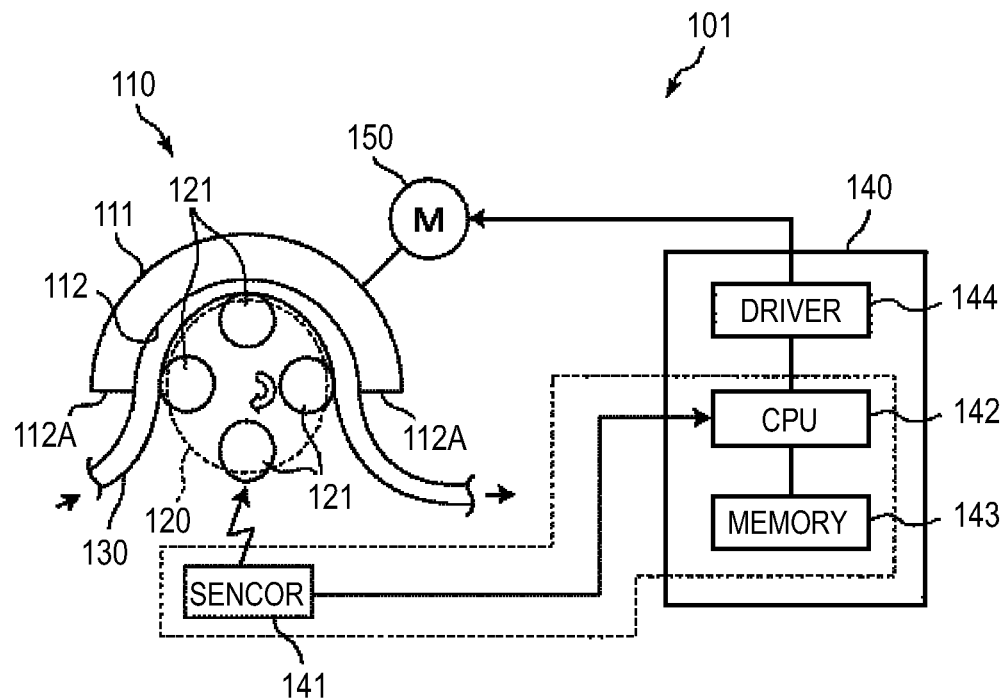
FIG. 6 is a diagram illustrating a peristalic pump which is a specific example of a solution pulsating unit.

Next, a related-art peristaltic pump (see JP-A-2004-92537) will be described as a specific example of the solution pulsating unit 11, with reference to FIG. 6.

A peristaltic pump ejection amount controlling apparatus 101 has a housing 111. A rotor 120, a plurality of rollers 121, a tube 130, a controller 140, and a sensor 141 are disposed in the housing 111. The housing 111, the rotor 120, the plurality of rollers 121, and the tube 130 constitute a peristaltic pump. A motor case which is not shown is connected to the housing 111, and a motor 150 is disposed in the motor case which is not shown.

An inputting section which is disposed at a position where the user of the peristaltic pump can operate the pump, and which is not shown is connected to the controller 140, so that the user can input, through the inputting section, a desired ejection amount which is to be ejected by the peristalic pump 110.

The rotor 120 has a substantially disk-like shape, and is supported by the housing 111 so as to be rotatable about the axis of the housing. Four rollers 121 are disposed at positions in the vicinity of the circumference of the rotor 120, and supported by the rotor 120 so as to be rotatable about the axial center. The rotation axes of the four rollers 121 are positioned on the same circumference which is coaxial with the rotation axis of the rotor 120, and have positional relationships in which they are parallel to the rotation axis of the rotor 120. The rotation axes of the four rollers 121 are placed on the same circumference at regular intervals in the circumferential direction. The circumferential surfaces of the rollers 121 are projected from the circumference of the rotor 120, toward the radial outward direction of the rotor 120.

An arcuate wall portion 112 is disposed in a part of the housing 111 and at a position opposed to a part of the circumference of the rotor 120. The arcuate wall portion 112 is approximately semicircularly disposed along the circumference of the rotor 120, and the position of the center of the arc coincides with the rotation axis of the rotor 120. The arcuate wall portion 112 is disposed so as to cover the upper half of the rotor 120 in FIG. 6. When the four rollers 121 are positioned respectively in the upper, lower, right, and left sides as shown in FIG. 6, the three or upper, right, and left rollers 121 are opposed to the arcuate wall portion 112, and two end portions 112A, 112A of the arcuate wall portion 112 are in positional relationships in which they are opposed to the right and left rollers 121, respectively.

The circumferential surfaces of the rollers 121 which are projected from the circumference of the rotor 120, toward the radial outward direction of the rotor 120 are separated from the arcuate wall portion 112 by a predetermined distance, and the tube 130 is disposed in the gap therebetween. The tube 130 is elastically deformable in a radial direction, and, in a state where it is wound around the rotor 120, immovable with respect to the housing 111. The distance between the circumferential surfaces of the rollers 121 and the arcuate wall portion 112 is shorter than the outer diameter of the tube 130 in a state where it is not elastically deformed. Therefore, the tube 130 is clamped between the arcuate wall portion 112 and the circumferential surfaces of the rollers 121 which are projected from the circumference of the rotor 120, toward the radial outward direction of the rotor 120, to be in a state where the tube is radially squeezed. By contrast, the portion of the tube 130 which is not clamped between the arcuate wall portion 112 and the circumferential surfaces of the rollers 121 is not elastically deformed. When the rotor 120 is rotated, the positions where the circumferential surfaces of the rollers 121 are opposed to the arcuate wall portion 112 are changed, and a fluid in the tube 130 is pushed out from the tube 130, whereby a reagent or a like fluid is ejected to a dispensing apparatus which is connected to the tube 130, and which is not shown.

Figure 7:
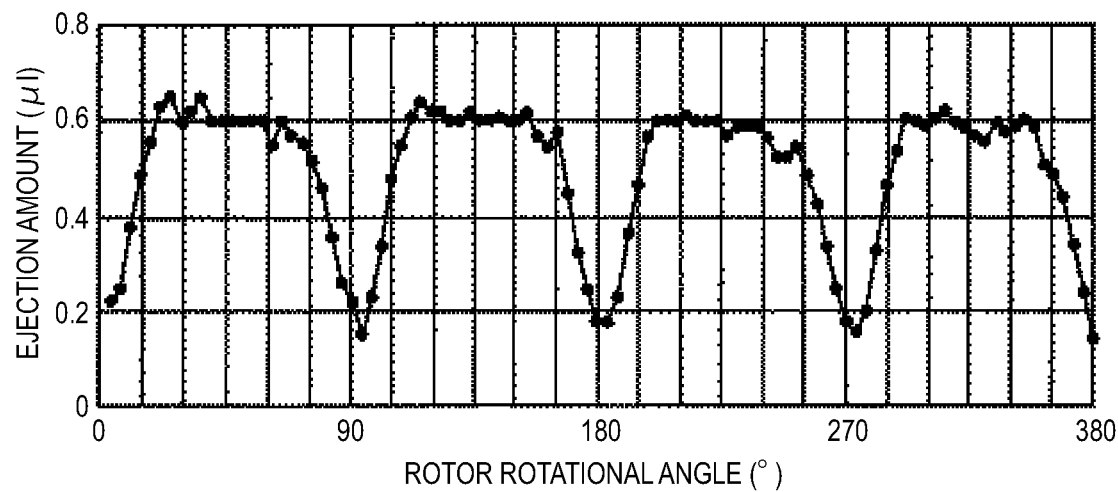
FIG. 7 is a view showing a change of the ejection amount of the peristalic pump of FIG. 6.

The rotor 120 is drivenly coupled to the motor 150, and coupled directly to the motor 150 so as to attain the same rotation amount. In accordance with the rotation of the rotor 120, the four rollers 121 are swung (revolve about the axis of the rotor 120) while being rotated. More specifically, the motor 150 is a stepping motor, and connected to the controller 140. The controller 140 has a central processing unit (CPU) 142, a memory 143 configured by a RAM and a ROM, and a driver 144. The CPU 142 controls the rotational speed and angle of the motor 150 via the driver 144. The CPU 142 is connected to the sensor 141 which is configured by an encoder, so that the CPU 142 always knows the rotational positions of the rollers 121 via the sensor 141. In the ROM of the memory 143, data of the ejection amount such as shown in FIG. 7 and inherent in the rotational positions of the rollers 121 on the rotor 120 are stored. When the peristalic pump 110 is to eject a desired amount, the CPU 142 calculates the rotational angle of the rotor 120 which is required for ejecting the desired amount, based on the rotational positions of the rollers 121 which are detected by the sensor 141, and the data of the ejection amount stored in the ROM of the memory 143, and controls the rotational angle of the motor corresponding to the rotational angle of the rotor 120. The sensor 141, the memory 143, and the CPU 142 correspond to a rotor rotational angle controlling unit.

Hereinafter, the pulsation flow which is shown in the graph of FIG. 7, and which is produced by the peristalic pump 110 will be described. In the graph of FIG. 7, the rotor rotational angle of 0° shows a state where the four rollers 121 are positioned in the upper, lower, right, and left sides of FIG. 6, respectively. The rotor position in this state is set as the origin position. The motor 150 is driven from this state to continuously rotate the rotor 120 by a minute angle, and the ejection amount at each of the minute angles is measured. The graph of FIG. 7 shows a plot of ejection amounts which are sequentially obtained until the rotor 120 makes one rotation, i.e., the four rollers 121 return to their original positions. The four bumps shown in FIG. 7 are related to the number of the rollers 121. When the rotor 120 is rightward rotated by 90 degrees in FIG. 6, the roller 121 which is at the upper position in FIG. 6 is swung to the right position, and one bump which is shown between the rotor rotation angles of 0° to 90° in FIG. 7 is produced. When the rotor 120 is further rightward rotated by 90 degrees, similarly, the roller 121 which is at the right position in FIG. 6 is swung to the lower position, and one bump which is shown between the rotor rotation angles of 90° to 180° in FIG. 7 is produced. Also with respect to the rotor rotation angles of 180° to 270° and 270° to 360° in FIG. 7, bumps are similarly produced, with the result that four bumps are produced during one rotation of the rotor 120. Namely, the number of bumps corresponds to that of the rollers.

By the peristalic pump which can pulsate the ejection amount as shown in FIG. 7, the distance (in the figure, the to-be measured solution in a pH measuring vessel) between the unit shown in FIG. 1 and for emitting the light beams of the two wavelengths and the unit for receiving the light beams is physically pulsated.

In the embodiment, a peristalic pump is used as the solution pulsating unit 11. The solution pulsating unit is not restricted to this, and any mode such as a syringe pump or a centrifugal pump may be employed as far as it can pulsate a solution.

Alternatively, the pH measuring section (the light emitting elements and the light receiving element) may be attached to the tube in the embodiment. In the alternative, preferably, the tube may have rigidity which allows the tube to be displaced by the pulsation flow caused by the peristalic pump or the like, and may be transparent or translucent so that the light beams can transmit through the tube.

The pulsation by the solution pulsating unit 11 is not required to be always performed, and may be performed only when the pH is to be measured. Moreover, the pulsation may be preferably performed at a predetermined frequency (for example, the pulse rate of a human) at which the pulsation can be detected.

In the case where, in FIG. 1, the distance (in the figure, the to-be measured solution in the pH measuring vessel) between the unit shown in FIG. 1 and for emitting the light beams of the two wavelengths and that for receiving the light beams is physically pulsated by the peristalic pump functioning as a unit which can pulsate the ejection amount as shown in FIG. 7, the followings are obtained.

When it is assumed that there is no scattering, the followings are obtained from the Lambert-Beer law.

$A_{558} = \alpha_{558} \Delta L C$
$A_{430} = \alpha_{430} \Delta L C$ where
α: absorption coefficient
ΔL: changing amount of optical path length
C: concentration Therefore, the absorbance ratio is expressed as follows.

$$A_{558}/A_{430} = \alpha_{558} \Delta L C / \alpha_{430} \Delta L C = \alpha_{558}/\alpha_{430}$$

According to the pH measuring apparatus (method) of the invention, as described above, the pH can be calculated from relationships of a pH and an absorption coefficient ratio which are previously obtained, without correction of the zero level due to a wavelength in the vicinity of 700 nm at which little absorption by the indicator is shown.

Next, the configuration shown in the block diagram of FIG. 1 illustrating the solution pH measuring apparatus of the invention will be described with reference to FIG. 8.

The light emitting elements (LEDs) 1, 2 which emit light beams of different wavelengths are driven by the driving circuit 3 so as to alternately emit the light beams by using the electric power supplied from the battery 4.

Figure 8:
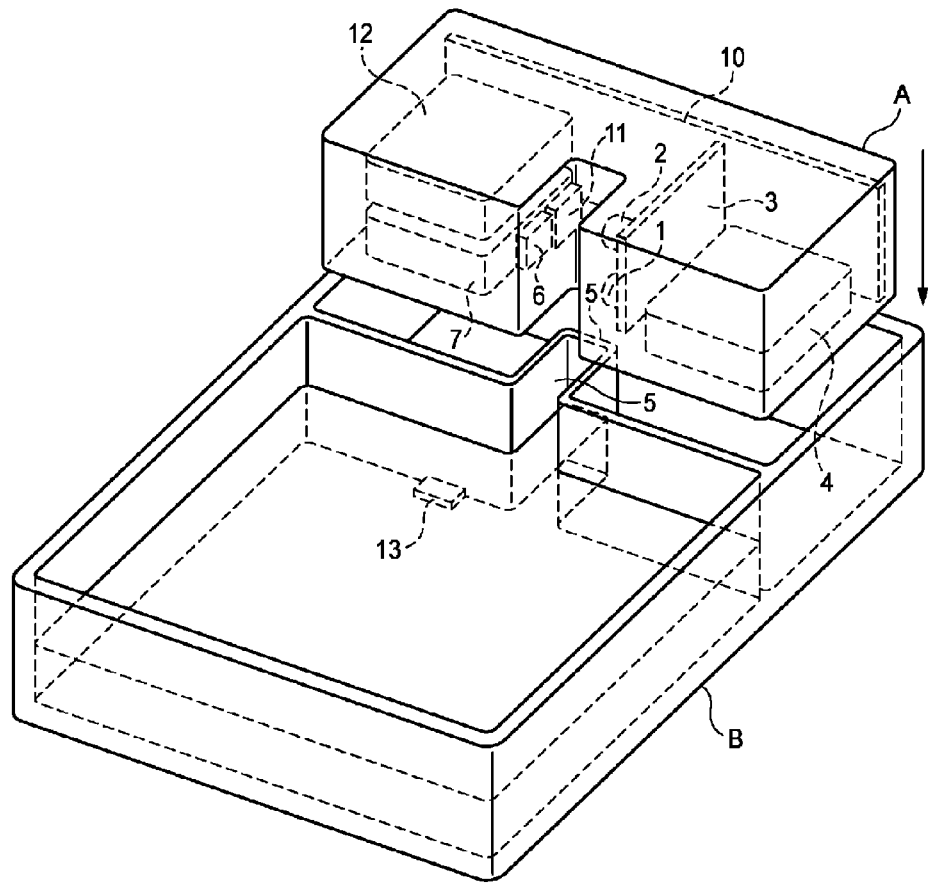
FIG. 8 is a view showing an example in which the apparatus for measuring the pH of a solution according to the invention is applied to a specific culture dish having a pH measuring apparatus which is to be carried on an incubator.
Figure 9:
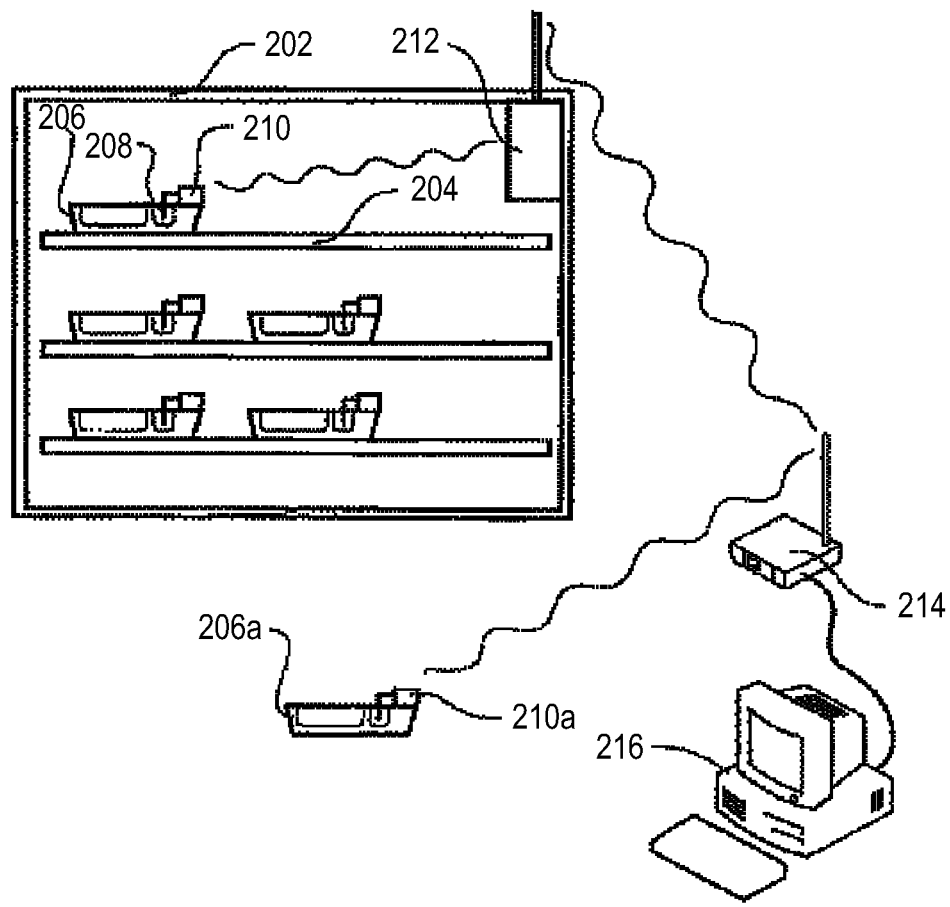
FIG. 9 is a view illustrating an incubator having trays on which related-art culture dishes are carried.
Figure 10:
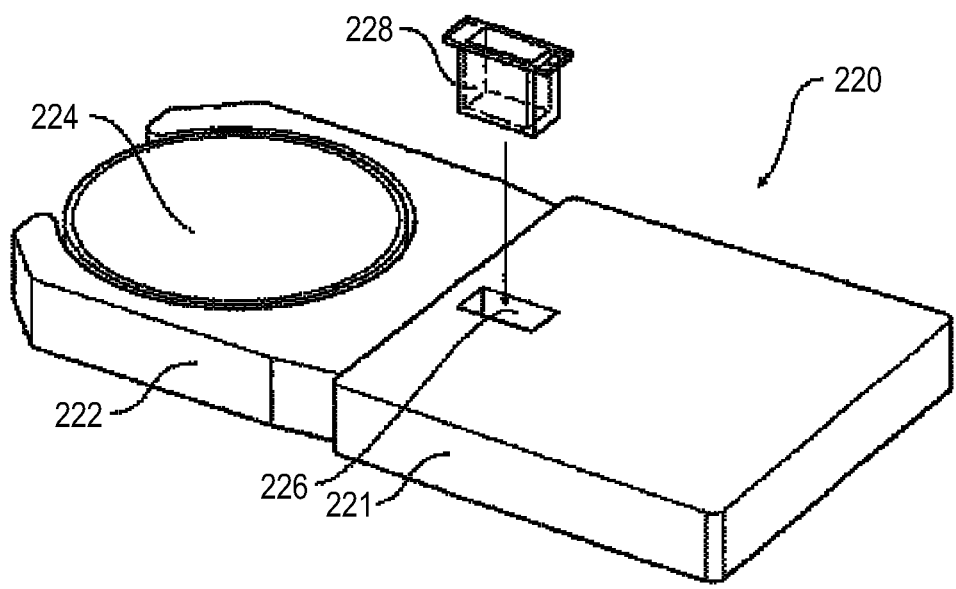
FIG. 10 is a view illustrating a related-art reader unit.
Figure 11:
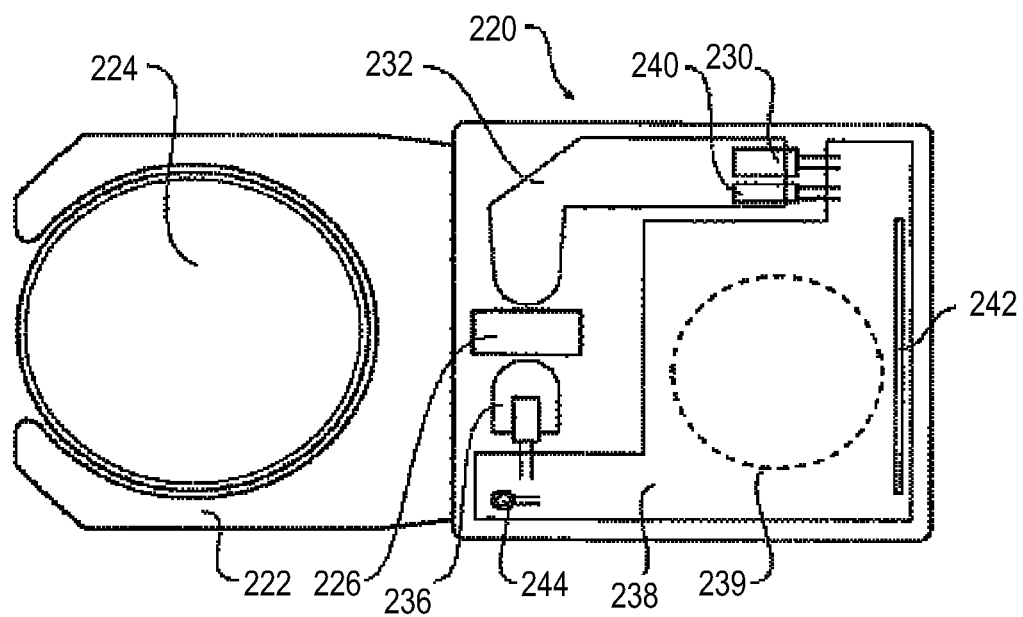
FIG. 11 is a view illustrating the configuration of the related-art reader unit.

A culture dish having a pH measuring apparatus shown in FIG. 8 is configured by a culture dish B and a pH measuring apparatus A. The pH measuring apparatus A is configured by a separate member so that the apparatus can be inserted in a manner that a pH measurement solution area in the culture dish is interposed between the light emitting elements (LEDs) and the light receiving element (PD).

The culture dish B is formed so that at least a part of the measurement solution which is in the culture dish, and into which the indicator is mixed can flow into the pH measurement solution area.

As the light beams of the light emitting elements 1, 2, those of wavelengths of 430-nm- and 558-nm- which indicate absorbance peaks are employed, respectively.

The light beams emitted from the light emitting elements 1, 2 are transmitted through the portion where the pH measurement solution 5 is placed, and then received by the photodiode (PD) 6 which is a light receiving element, to be converted to electric signals.

Then, the converted signals are amplified by the amplifier 7, noise components are reduced by the multiplexer and the filters which correspond to the light wavelengths, and the signals are then digitized by the A/⊃ converter which is not shown, and thereafter supplied to the processing section (CPU) 10.

The reference numeral 11 denotes the solution pulsating unit for physically pulsating the distance (in the figure, the to-be measured solution in the pH measuring vessel) between the unit for emitting the light beams of the two wavelengths and the unit for receiving the light beams.

As the solution pulsating unit, a unit which is juxtaposed with the light receiving element (PD) or the light emitting elements (LEDs), and which periodically performs a pressing operation to physically pulsate the distance (in the figure, the to-be measured solution in the pH measuring vessel) between the light beam emitting unit and the light beam receiving unit is more suitable than the above-described peristalic pump.

According to an aspect of the invention, it is possible to realize a method and apparatus for measuring the pH of a solution in which it is not necessary to correct the zero level due to a wavelength in the vicinity of 700 nm that shows very little absorption by an indicator.

What is claimed is:

1. A method of measuring a pH of a solution comprising:
   emitting light beams of two wavelengths from one side of a measuring region of a solution into which an indicator is mixed, while pulsating the solution in the measuring region;
   receiving at least one of transmitted light beams and reflected light beams of the emitted light beams on the other side of the measuring region, while pulsating the solution in the measuring region;
   obtaining absorbances of the two wavelengths based on variations of the received at least one of the transmitted light beams and the reflected light beams, the variations due to the pulsation of the solution in the measuring region;
   obtaining an absorbance ratio from the obtained absorbances; and
   calculating a pH value of the solution based on the obtained absorbance ratio and an absorbance ratio/pH value correspondence database which is previously stored.

2. The method according to claim 1, wherein one of the light beams has a wavelength of 400 to 460 nm, and the other of the light beams has a wavelength of 530 to 580 nm.

3. An apparatus for measuring a pH of a comprising:
   a light source configured to emit light beams of two wavelengths from one side of a measuring region of a solution into which an indicator is mixed;
   a light receiving sensor configured to receive at least one of transmitted light beams and reflected light beams of the emitted light beams on the other side of the measuring region;
   a pump configured to perform pulsation of the solution in the measuring region; and
   a CPU processing section configured to receive data from the light receiving sensor and to process the received data to:
   (i) obtain absorbance of the two wavelengths based on variations of the at least one of the transmitted light beams and the reflected light beams which are received by the light receiving sensor during the pulsation of the solution by the pump, the variations due to the pulsation of the solution in the measuring region;
   (ii) obtain an absorbance ratio from the obtained absorbances; and
   (iii) calculate a pH value of the solution based on the obtained absorbance ratio and an absorbance ratio/pH value correspondence database which is previously stored.

4. The apparatus according to claim 3, wherein the pump performs the pulsation of the solution existing between the light source and the light receiving sensor.

5. The apparatus according to claim 3, wherein the pump is one of a peristalic pump, a syringe pump, and a centrifugal pump, placed in front of or in back of the measuring region of the solution.

6. The apparatus according to claim 3, wherein the pump performs the pulsation at a frequency at which pulsation can be detected.

7. The apparatus according to claim 3, wherein the pump performs the pulsation only when the pH is to be measured.

8. The apparatus according to claim 3, wherein the pump changes a distance between the light source and the light receiving sensor.

* * * * *